United States Patent [19]
Fujita et al.

[11] Patent Number: 5,981,668
[45] Date of Patent: Nov. 9, 1999

[54] ANTI-BACTERIAL WATER ABSORBING AGENT AND ANTI-BACTERIAL WATER ABSORBENT MATERIAL

[75] Inventors: Masahisa Fujita, Kyoto; Masanori Koike, Tokai; Kenjiro Tsubota, Kyoto, all of Japan

[73] Assignee: Sanyo Chemical Industries, Ltd., Japan

[21] Appl. No.: 08/958,440

[22] Filed: Oct. 27, 1997

[30] Foreign Application Priority Data

Oct. 31, 1996 [JP] Japan ................................. 8-307359

[51] Int. Cl.$^6$ ....................................................... C08F 8/30
[52] U.S. Cl. ..................... 525/329.9; 525/330.2; 525/327.6; 525/328.5; 525/326.6
[58] Field of Search .............. 525/329.9, 330.2, 525/327.6, 328.5, 326.6

[56] References Cited

U.S. PATENT DOCUMENTS 5,563,201  10/1996  Joanicot et al. ..................... 524/425

FOREIGN PATENT DOCUMENTS

| | | |
|---|---|---|
| 56-31425 | 3/1981 | Japan . |
| 57-25813 | 2/1982 | Japan . |
| 59-179114 | 10/1984 | Japan . |
| 59-189854 | 10/1984 | Japan . |
| 60-158861 | 8/1985 | Japan . |
| 417058 | 1/1992 | Japan . |
| 5179053 | 7/1993 | Japan . |

*Primary Examiner*—Edward J. Cain
*Attorney, Agent, or Firm*—Doylance, Abrams, Berdo & Goodman

[57] ABSTRACT

An anti-bacterial water absorbing agent having excellent water absorption, anti-bacterial activity, and powder flow properties. The agent is useful in the manufacture of absorbent materials particularly for absorbing urine, blood, and body fluids and the like. The agent comprises a water absorbing resin (A) having pendant acid groups, at least on acid group being in the form of a quaternary ammonium salt having the general formula (1).

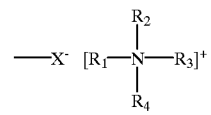

(1)

wherein $-X^-$ is an anionic pendant group covalently bonded to backbone in the water absorbing resin (A) and $R_1$, $R_2$, $R_3$, and $R_4$ are organic groups. In embodiments, at least one of the organic groups on the ammonium ion is an aliphatic alkyl group having 5 to 20 carbons. At least one of $R_1$, $R_2$, $R_3$ and $R_4$ is a $C_5$ to $C_{20}$ aliphatic alkyl group. The resin has a quaternary nitrogen atom content of about $2 \times 10^{-4}$% to about 0.8% by weight.

23 Claims, No Drawings

ANTI-BACTERIAL WATER ABSORBING AGENT AND ANTI-BACTERIAL WATER ABSORBENT MATERIAL

BACKGROUND OF THE INVENTION

1. Field of the Invention

The present invention relates to an anti-bacterial water absorbing agent which has excellent water absorption performance, anti-bacterial performance, and powder flow properties. The anti-bacterial water absorbing agent is suitable for the manufacture of absorbent materials for absorbing urine, blood, and body fluids. The invention is further directed to a method of producing said agent and an absorbent material using said agent.

2. Description of the Related Art

Water absorbing resins are widely used in absorbent materials or absorbing articles including disposable diapers, incontinence pads, sanitary napkins, nursing pads, sheets for pets, absorbent materials for pets littex, excretion treating agents, waste blood gelling materials, drip absorbers, and freshness retaining materials. These devices rely on the water absorption/retention capacities and gelling properties of the resin. Although the conventional water absorbing resins have excellent absorption/retention capacities for urine, blood, and other body fluids, these prior materials do not have anti-bacterial properties.

Therefore, when the water absorbing resin absorbs urine, blood, and other body fluids, the organic materials contained in the liquids being absorbed are degraded by bacteria, fungus and other microorganisms, thereby causing, for example, malodors, skin irritations, and rashes. Furthermore, the resulting hydrogels are also easily putrefied by the bacteria in the air resulting in the development of odors. To overcome these problems, materials which exhibit both absorption and anti-bacterial properties are desired to provide a hygienic and safe environment. The development of odors and rashes is a serious problem in absorbent materials such as disposable diapers for the bedridden elderly and the sick, so that an early solution to the problem is desired.

Several materials have been proposed for controlling odor and bacterial growth in absorbent materials. One example is a powder mixture of a water absorbing resin and a zeolite as disclosed in Japanese Kokai Nos. 57-25813, 59-179114, and 59-189854. Another example includes a composition of activated carbon coated with a water absorbing resin as disclosed in Japanese Kokai No. 56-31425. A further composition consisting of a water absorbing resin and a deodorant component extracted from camellia is disclosed in Japanese Kokai No. 60-158861. A water absorbing resin composition containing a specific anti-bacterial agent of benzalkonium chloride, chlorhexidine gluconate, and various phosphates is disclosed in Japanese Kokoku No. 4-17058, and Kokai No.5-179053. These compositions have been proposed for use in the manufacture of absorbent materials.

However, these prior compositions are not entirely satisfactory in controlling odors and preventing putrefaction of fluids in an absorbent material. These water absorbing resins require treatment with an anti-bacterial compound to provide anti-bacterial and deodorant activity. In addition, the powder flow property is degraded by the treatment which is necessary to provide the anti-bacterial and deodorant activity.

The prior compositions which include a mixture of a water absorbing resin and a zeolite can adsorb some odors. However, since neither the water absorbing resin nor the zeolite have anti-bacterial effect, the composition cannot suppress putrefaction of organic materials caused by bacteria, fungus or other microorganism, and cannot suppress the development of odors. In addition, the conventional absorbent materials cannot prevent the occurrence of skin irritations and rashes. The separation of the zeolite from the water absorbing resin by shaking or impacting increases the likelihood of dust particles becoming airborne. In addition there is a wide variation in the odor control activity of the resulting composition.

Compositions of activated carbon coated with a water absorbing resin and compositions consisting of a water absorbing resin and a deodorant component extracted from camellia, are also not able to suppress putrefaction of organic materials caused by microorganisms and fungus, since the activated carbon and the deodorant component extracted from camellia have no anti-bacterial activity.

A water absorbing resin compound containing a benzalkonium chloride, chlorhexidine gluconate, or phosphate exhibits anti-bacterial effect to some extent, but generally is not satisfactory. This composition has limited effectiveness in controlling or suppressing the growth of certain kinds of bacteria, fungus and other microorganisms. Further, the powder flow property of the water absorbing resin treated with the anti-bacterial agent is considerably reduced depending on the amount of the anti-bacterial agent used.

Furthermore, special steps or operations are required to fix a zeolite, activated carbon, or a deodorant extracted from camellia to the water absorbing resin. Accordingly, a need exists for improved water absorbing compositions having water absorbent and anti-bacterial properties.

SUMMARY OF THE INVENTION

The present invention is directed to an anti-bacterial water absorbing agent having excellent water absorption performance, anti-bacterial activity, and powder flow properties. The invention is further directed to water absorbent materials particularly for absorbing urine, blood, other body fluids and the like. A further aspect of the invention is directed to a method for preparing a water absorbing resin for the anti-bacterial water absorbing agent.

The anti-bacterial water absorbing agent of the present invention includes a water absorbing resin (A) having pendent acid groups, and at least one acid group is in the former of a quaternary ammonium salt. The resin has a quaternary nitrogen atom content of from $2 \times 10^{-4}\%$ to $0.8\%$ by weight based on the weight of said resin (A). The resin is particularly suitable in the manufacture of absorbent materials having a layer of the water absorbing agent of the invention retained in a water absorbent substrate.

Accordingly, a primary object of the invention is to provide a water absorbing agent having anti-bacterial activity.

A further object of the invention is to provide an anti-bacterial absorbing agent comprising a resin having anti-bacterial properties together with water absorption properties, by reacting a water absorbing resin and a quaternary ammonium compound.

Still another object of the invention is to provide an anti-bacterial water absorbent material having a layer of the water absorbing agent of the present invention retained in a water absorbent substrate.

The objects of the invention are basically attained by providing an anti-bacterial water absorbing agent comprising a water absorbing resin, having pendent acid groups, at least one acid group being in the form of a quaternary ammonium salt, said resin (A) having a quaternary nitrogen atom content of about $2 \times 10^{-4}\%$ to about 0.8% by weight based on the weight of said resin (A).

The objects of the invention are further attained by providing a method of producing a water absorbing resin (A) for an anti-bacterial water absorbing agent comprising the steps of reacting a water absorbing resin (a) having pendant acid groups with a quaternary ammonium carbonate (b) in the presence of water to produce said water absorbing resin (A) having pendant acid groups, at least one said acid group being in the form of a salt, quaternary ammonium and said resin (A) having a quaternary nitrogen atom content of about $2 \times 10^{-4}\%$ to about 0.8% by weight based on the weight of said resin (A).

The objects of the invention are also attained by providing a method of a water absorbent material comprising: a water absorbent substrate; and an anti-bacterial water absorbing agent on the substrate, said anti-bacterial water absorbing agent comprising a water absorbing resin (A) having pendent acid groups, at least one acid group being in the form of a quaternary ammonium salt, wherein said resin (A) has a quaternary nitrogen content of about $2 \times 10^{-4}\%$ to about 0.8% by weight based on the weight of said resin(A).

These and other objects, advantages, and salient features of the invention will become apparent from the detailed description of the invention which disclose preferred embodiments of the invention.

DETAILED DESCRIPTION OF THE INVENTION

The present invention is directed to a water absorbing agent which exhibits anti-microbial and particularly anti-bacterial activity. More particularly, the invention is directed to an anti-bacterial water absorbing agent comprising a water absorbing resin (A) suitable for use in producing water absorbent materials.

The water absorbing resin (A) has pendent acid groups. At least one acid group is in the form of a quaternary ammonium salt.

Said resin (A) can be derived from a water absorbing resin (a) having pendant acid groups.

A number of water absorbing resins having pendant acid groups are suitable for the water absorbing resin (a). Examples of suitable pendant acid groups include carboxyl groups, sulfonic groups, sulfuric groups, and phosphoric groups. The acid groups may be partially neutralized. In this case, at least one group of the resin (a) reacts with (b) to form said resin (A). In preferred embodiments, the water absorbing resin (a) have a carboxyl group, a sulfonic group, or a phosphoric group as discussed hereinafter in greater detail.

Examples of the water absorbing resin (a1) having a carboxyl group preferred for use in the present invention include:

crosslinked copolymers of starch-acrylic acid acrylates, as disclosed in Japanese Kokoku Nos. 53-46199 and 53-46200;

selfcrosslinked polyacrylates and salts thereof or crosslinked polyacrylates and salts thereof obtained by reversed-phase suspension polymerization, as disclosed in Japanese Kokoku No. 54-30710, Kokai No. 56-26909;

crosslinked polyacrylic acid or polyacrylates obtained by aqueous solution polymerization, such as adiabatic polymerization, thin-film polymerization, and spray polymerization, as disclosed in Japanese Kokai No. 55-133413;

saponificated copolymers of vinyl esters and unsaturated carboxylic acid or the derivatives thereof, as disclosed in Japanese Kokai Nos. 52-14689 and 52-27455;

crosslinked copolymers of isobutylene-maleic acid anhydride, hydrolyzates of crosslinked copolymers of starch-acrylonitrile, crosslinked carboxymethylcellulose derivatives, and crosslinked copolymers of acrylic acid acrylate-acrylamides.

In embodiments of the invention, two or more of these water absorbing resins may be used in combination. The surface-crosslinked water absorbing resin obtained by crosslinking the surface of the powdery polymer with a crosslinking agent is also preferable for use in the present invention.

An example of a water absorbing resin (a2) having a sulfonic group includes a crosslinked polyacrylic acid polyacrylate prepared by the copolymerization of a monomer containing a sulfonic group as disclosed in Japanese Kokai Nos. 58-2312 and 61-36309.

Examples of suitable monomers having a sulfonic group for producing the water absorbing resin in which some of the carboxylic acid groups are substituted with the monomers having a sulfonic group include aliphatic or aromatic vinyl sulfonic acids, such as vinylbenzene sulfonic acid, alkyl sulfonic acid, vinyltoluene sulfonic acid, and styrene sulfonic acid, (meth)acrylic sulfonic acids, such as sulfoethyl (meth)acrylate and sulfopropyl (meth)acrylate, and (meth)acrylamidosulfonic acids, such as 2-acrylamide-2-methylpropane sulfonic acid.

Examples of the water absorbing resin (a3) having a phosphoric group include a water absorbing resin in which some carboxylic acids of the crosslinked polyacrylic acid (or polyacrylate) described above are substituted with monomers having a phosphoric group. Specific examples of the monomer having a phosphoric group include methacryloidoxyethyl phosphate and acryloidoxyethyl phosphate.

The water absorbing resin (a1) having carboxyl groups are preferable for use in the present invention. The water insoluble, water absorbing resins containing an acrylic acid and an acrylate as the resin constituent monomeric units are more preferable since these polymers exhibit a relatively large water absorption capacity and have excellent reactivity for forming quaternary ammonium salts.

The salts prepared by neutralizing the acid groups in the water absorbing resin (a) normally produce a sodium salt and/or a potassium salt. Alternatively, the acid groups can be neutralized with an organic acid such as an ammonium salt and an amine salt depending on the application.

In the water insoluble, water absorbing resin containing neutralized groups, the ratio of the carboxyl groups to the total amount of the carboxyl groups and the carboxylate groups are preferably about 20 to about 50 mole %, more preferably about 25 to about 40 mole %. The free carboxyl groups water in the absorbing resin (a) contains which do not form quaternary ammonium salts, may absorb ammonia, and thus, function as an odor absorbent.

When the molar ratio of the carboxyl groups to the total amount of the carboxyl groups and the carboxylate groups is above 50 mole %, the water absorption performance is reduced, and the pH of the resultant anti-bacterial water absorbing agent falls in the acidic range. The agent having an acidic pH is undesirable when the agent is intended to contact the skin.

The molar ratio of the carboxyl groups is preferably at least 20 mole %, since below 20 mole % the absorption of ammonia or the ammonium and amine compounds becomes poor and the pH of the resultant anti-bacterial water absorbing agent falls in the alkaline range. The alkalinity typically may result in skin irritation.

In the present invention, the water absorbing resin (A) contains quaternary ammonium groups in the form of a quaternary ammonium salt coupled to the at least one pendant acid group of the resin. The resin (A) has the water absorption capability of a water absorbing resin (a) and the anti-bacterial performance of a quaternary ammonium group containing anti-bacterial compound.

The pendant acid group in the form of quaternary ammonium salt is represented by the following general formula (1).

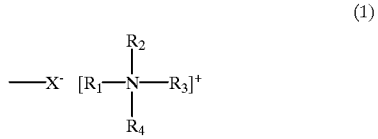

wherein $X^-$ is a pendant anionic group covalently bonded to a polymer backbone in the water absorbing resin (A), and $R_1$, $R_2$, $R_3$ and $R_4$ are organic groups; and at least one of $R_1$, $R_2$, $R_3$ and $R_4$ is a $C_5$ to $C_{20}$ aliphatic alkyl group.

The pendant anionic group —$X^-$ is not particularly limited so long as it is capable of functioning as a counterion of a quaternary ammonium cation, to form a quaternary ammonium salt. $X^-$ includes, for example, a carboxyl anion group (COO$^-$), a sulfonic anion group (—SO$_3^-$), a sulfuric anion group, and a phosphoric anion group. A carboxyl anion group and a sulfonic anion group are preferable with the carboxyl group anion being most preferable.

$R_1$, $R_2$, $R_3$, and $R_4$ are preferably hydrocarbon groups, and particularly aliphatic alkyl groups. In preferred embodiments at least one of $R_1$, $R_2$, $R_3$, and $R_4$ is a $C_5$ to $C_{20}$ alkyl group with the remaining groups being lower alkyl groups, such as, for example, methyl, ethyl or propyl group.

The amount of the quaternary ammonium group in the form of a salt in the water absorbing resin calculated in terms of quaternary nitrogen atom, is typically about $2 \times 10^{-4}\%$ to about 0.8% by weight, preferably within a range from about $1 \times 10^{-3}\%$ to 0.4% by weight, most preferably within a range from about $2 \times 10^{-3}\%$ to about 0.1% by weight based on the weight of the resin.

The water absorbing resin (A) is preferably in the form of particles or beads. The resin particles can have any desirable shape as known in the art. In embodiments, the resin can have, for example, a grainy shape, a granular shape, an agglomerated shape, a scaly shape, a lumpy shape, a pearly shape, or an impalpable powdered shape. A grainy shape, a granular shape, an agglomerated shape, a scaly shape, and a lumpy shape are most preferable. Also, the particle size and the particle size distribution are not particularly limited. Preferably, the diameter of about 90 wt. % or more of the particles is about 1 mm or less. Most preferably, the diameter of about 90wt. % or more of the particles is from about 0.1 mm to about 0.9 mm.

The absorbency of the water absorbing resin (A) is determined by the absorbency to physiological saline solution consisting of an aqueous solution of 0.9% sodium chloride. Preferably, the resin (A) has an absorbency of about 30 g/g or more, more preferably 35 to 80 g/g, and most preferably 40 to 75 g/g. The absorbency is measured by using a method described below.

The anti-bacterial water absorbing resin is prepared by, for example, reacting a water absorbing resin (a) having pendent acid groups with a quaternary ammonium carbonate compound (b) in the presence of water. The reaction proceeds by the anion-exchange between the carbonate anions and the cation of the pendent acidic anion, whereby the pendent acidic anion become the counter ion of the quaternary ammonium cation in the ammonium carbonate compound (b). This reaction has an advantage that the carbonate anion vaporizes during the reaction to produce a highly pure reaction product of the resulting water absorbing resin (A) without the production of acid by-products.

In the present invention, the molar ratio of the resin (a) to the quaternary ammonium carbonate compound (b) is not particularly limited so long as the amount of the quaternary nitrogen atom falls within the range defined above. The ratio can be varied depending on the balance between the desired absorption performance and the anti-bacterial performance and the type of compound (b). The ratio of the equivalents of the acid groups in the resin (a) and the equivalents of the quaternary ammonium carbonate (b), is typically about 1 to (between about $3 \times 10^{-5}$ and 0.3), preferably 1 to (between about $1 \times 10^{-4}$ and 0.1), more preferably 1 to (between about $3 \times 10^{-4}$ and $8 \times 10^{-2}$).

When the above-mentioned equivalent ratio of the quaternary ammonium carbonate (b) is less than $3 \times 10^{-5}$ per equivalent of the acid groups, the anti-bacterial effect of the resultant agent is insufficient. An equivalent ratio of the quaternary ammonium carbonate (b) of 0.3 per equivalent of the acid groups, produces an effective anti-bacterial activity in the resulting agent. The anti-bacterial effect of the resin (A) is unchanged when the equivalent ratio of the quaternary ammonium carbonate is more than 0.3, but the water absorption performance decreases. Consequently, in order to maintain the water absorption and anti-bacterial effect at a predetermined level in the manufacture of absorbent materials, it is necessary to use a large volume of the resulting water absorbing resin (A), thereby increasing the costs.

The quaternary ammonium carbonate compound having groups of $R_1$, $R_2$, $R_3$, and $R_4$ described above, can be used as the quaternary ammonium carbonate compound (b) to produce the anti-bacterial water absorbing resin. The quaternary ammonium carbonate compound (b) can be prepared, for example, by the reaction between tertiary amine (b1) containing at least one aliphatic alkyl group having 5 to 20 carbon atoms and diester carbonate (b2).

The suitable examples of tertiary amine (b1) include octyl dimethylamine, decyl dimethylamine, lauryl dimethylamine, myristyl dimethylamine, cetyl dimethylamine, stearyl dimethylamine, dihexyl methylamine, dioctyl methylamine, didecyl methylamine, and didodecyl methylamine. The tertiary amine having two aliphatic alkyl groups of 5 to 20 carbon atoms is preferable, and dioctyl methylamine and didecyl methylamine are more preferable.

The suitable examples of diester carbonate (b2) include dimethyl carbonate, diethyl carbonate, ethylmethyl carbonate, and dipropyl carbonate. Diester carbonates having alkyl groups with fewer carbon atoms are more reactive than the ones having long chain alkyl groups and, therefore, dimethyl cabonate is preferable.

In preparation of the quaternary ammonium carbonate compound (b), the molar ratio of tertiary amine (b1) to diester carbonate (b2) can vary depending on the reactants. Typically, about 0.3 to 4.0 moles and preferably about 0.5 to 2.5 moles of the diester carbonate (b2) is reacted with one mole of the tertiary amine (b1). The reaction temperature is typically from about 30° C. to 150° C., preferably from about 50° C. to 120° C. The solvent, such as methanol or ethanol, or mixture of such alcohols with water, can be used as required.

The specific methods for reacting the water absorbing resin (a) with the quaternary ammonium carbonate compound (b) in the presence of water include the following preferred methods:

(1) reacting (a) with (b) by treating the surface of particles or powders of the water absorbing resin (a) with an aqueous solution of a quaternary ammonium carbonate compound (b).

(2) kneading the hydrogel of water absorbing resin (a) obtained in the polymerization process and a quaternary ammonium carbonate compound (b) in a kneading machine, followed by heating to react and dry the mixture, and grinding the resultant product.

(3) mixing water and the water absorbing resin (a) whereby the resin (a) absorbs water to form a hydrogel, followed by kneading the hydrogel and the quaternary ammonium carbonate (b) in a kneading machine, heating to react and dry the mixture, and grinding the resulting resin.

(4) preparing a hydrogel by allowing the water absorbing resin (a) to absorb an aqueous solution of the quaternary ammonium carbonate compound (b), followed by kneading the resulting hydrogel-forming mixture in a kneading machine, and then heating to react and dry the hydrogel-forming, and grinding the resulting resin.

Preferable methods among these (1)–(4) are (1) and (4).

The amount of water used to produce the anti-bacterial water absorbing resin in the method (1)–(4) is typically from 1 to 500 parts by weight to about 100 parts by weight of the water absorbing resin (a), and preferably from 5 to 450 parts by weight. When the amount of water is less than 1 parts by weight, the reaction of the water absorbing resin (a) and the quaternary ammonium compound (b) does not sufficiently proceed. When the amount of water exceeds 500 parts by weight, the reaction of the water absorbing resin (a) and the quaternary ammonium compound (b) is not hindered, but it is necessary to evaporate a large volume of water after the reaction, thereby increasing the manufacturing costs.

In the methods (1)–(4), there is no particular limitation for an industrial apparatus used in mixing the components (a) and (b) so that well-known conventional apparatus can be used. Examples of the industrial apparatus used in mixing the powders of a water absorbing resin (a) and the aqueous solution of a quaternary ammonium compound (b) include a universal mixer, a turbulizer, a Nauta blender, a ribbon blender, a conical blender, a V-shaped mixer, and a screw mixer. The examples of the industrial apparatus used in kneading the hydrogel of (a) with (b) include a kneader, a screw extruder, a double-screw extruder, an universal mixer, a Nauta blender, and a screw mixer.

The temperature of reacting the water absorbing resin (a) and the quaternary ammonium compound (b) is not particularly limited. The reaction temperature is preferably from about 0 to about 150° C., more preferably from about 10 to 130° C. when the water absorbing resin is in a powdered state.

The reaction temperature is preferably maintained at about 40° C. to 150° C., and more preferably at about 40° C. to 130° C. when the water absorbing resin is hydrated to form a gel. It is generally necessary to dry the hydrated, gelled resin by using the heat of reaction. A reaction temperature of at least 0° C. is desirable to prevent the water from freezing. Temperatures above about 150° C. are also not desirable since some quaternary ammonium compounds degrade at high temperature.

The anti-bacterial water absorbing agent of the present invention can be optionally contained together with said resin (A), organic powders such as a bulk filler, an additive such as pulp powders, cellulose derivatives, natural polysaccharides and the like; inorganic absorbent powders, such as silicon dioxide, aluminum oxide, magnesium oxide, aluminum silicate, sodium silicate, and magnesium silicate and the like; and other additives such as anti-oxidants, surfactants, deodorants, coloring agents, perfumes and the like. The amount of these substances is typically about 10% by weight or less based on the weight of the water absorbing resin (A).

When applied to various absorbent materials, the anti-bacterial water absorbing agent of the present invention is satisfactory in both water absorption and anti-bacterial effects. The anti-bacterial water absorbing agent can be applied to an absorbent material by any method where the anti-bacterial water absorbing agent is retained in a water absorbent substrate to form a layer. An example of a suitable method includes scattering the anti-bacterial water absorbing agent between two layers of pulp or fibrous materials and, if necessary, fusing the layers together. Heat fusible materials or fibers can be disposed in the pulp or fibrous layers to assist in fusing the layers together. Alternatively, the anti-bacterial water absorbing agent can be mixed with pulp or fibrous materials such as heat fusible fiber and compressed to fuse the fibers together. The anti-bacterial water absorbing agent can also be sandwiched between two or more layer of water absorbent papers or non-woven fabrics and laminated the layers together. The amount of the anti-bacterial water absorbing agent combined with an absorbent material can be varied depending on the kind and the size of absorbent materials, and the desired absorbent performance.

Disposable diapers and incontinence pads are generally produced using from 3 to 20 grams of the anti-bacterial water absorbing agent per piece of the absorbent material. Alternatively, in the case of sanitary napkins, panty liners, and nursing pads, typically use from 0.2 to 3 grams of the anti-bacterial water absorbing agent per piece.

The amount of the anti-bacterial water absorbing agent is typically from 10 to 80 g/m$^2$, when sandwiched between two or more water absorptive papers or non-woven fabrics layers.

EXAMPLES

The present invention will be more specifically described with respect to the following examples and comparative examples. However, it should be understood that the present invention is not limited thereto. The absorbency and the anti-bacterial effect of the anti-bacterial water absorbing agent, and the evaluation for the absorbent materials employing the anti-bacterial water absorbing agent were measured by the following methods. All percentages are based on weight unless otherwise indicated.

(1) Absorbency

A tea bag of 250-mesh nylon net is charged with 1 g of a sample of anti-bacterial water absorbing agent, and immersed in an excess amount of physiological saline solution (0.9% NaCl aqueous solution) for 1 hour to absorb the solution. The bag is removed from the saline solution and allowed to drain by hanging for 15 minutes. Thereafter, the weight gain was measured. The weight gain is defined as the absorbency.

(2) Powder Flow Property

The powder flow property is evaluated by measuring the angle of repose. The angle of repose of the water absorbing resin is measured by using a Powder Tester (available from Hosokawa Micron, Japan). An appropriate amount of a sample water absorbing resin is gently placed in a sieve (710 micron mesh). The sieve is vibrated and tapped to allow the water absorbing resin to flow through the outlet of a glass funnel placed under the sieve. The angle of repose is measured by moving a protractor in such a way that the edge line of the pile of powder is parallel with the straight line of the protractor. The flow of the water absorbing resin is stopped when the edge line of the resulting pile of powder forms a predetermined angle.

(3) Anti-bacterial Test for the Anti-bacterial Water Absorbing Agent 3.45 g of sensitive buiyolln medium is dissolved in 150 ml of water charged into a 300 cc flask, followed by autoclave sterilization. 1 g of a test sample anti-bacterial water absorbing resin is added in the culture medium, then allowed to swell while stirring. E. coli is then inoculated onto the culture medium at a cell count of $1 \times 10^6$/ml.

The culture medium is shaken at 37° C. and the viable cell counts are measured after 2 hours and again after 10 hours. A stepwise dilution of the culture is carried out with sterilized water as required. The cell count is measured in accordance with a plate culture method. A blank test using only E. coli inoculated onto the medium showed a viable cell count of $5 \times 10^8$/ml after 2 hours, and $6 \times 10^9$/ml after 10 hours.

The anti-bacterial test with *Prodidencia vettgeri* is also carried out in a similar manner as in the E. coli case. A blank test, using only *Providencia vettgeri* inoculated onto the medium without a test sample showed a viable cell count of $8 \times 10^7$/ml after 2 hours, and $4 \times 10^9$/ml after 10 hours.

(4) Evaluation for the Absorbent Materials Employing The Anti-bacterial Water Absorbing Agent Preparation for the Absorbent Material:

A polyethylene sheet cut into a 14 cm×35 cm rectangle a sheet of tissue paper and a layer of fluff pulp having a unit density of 100 g/m² and placed in this order.

2.94 g of the sample are then uniformly scattered over the layer of fluff pulp, followed by placing an another fluff pulp layer having unit density of 100 g/m². A sheet of tissue paper, and a sheet of a non-woven fabric, respectively are then placed over the fluff pulp layer. The materials are laminated by pressing at 5 Kg/cm² for 90 seconds to obtain a model diaper.

Test for Bad Odor Suppressing Effect:

80 ml of fresh human urine are injected in the central part of the absorbent material employing the anti-bacterial water absorbing agent. The absorbent material is placed in a 5-liter wide-mouthed bottle, sealed, and stored in a thermostatic chamber controlled at 40° C. for 10 hours.

The bottle is then opened in an odorless room, and the odor generation is measured in accordance with the following 6-step evaluation. 10 panel members authorized to have odor decisive ability according to T & T olfactometer method evaluate the odor level, and the averages are taken.

0: odorless
1: barely sensible odor (sensible concentration)
2: recognizable faint odor (recognizable concentration)
3: easily recognizable odor
4: strong odor
5: irritating odor Absorption The absorbent material is immersed in excess physiological saline solution for 30 minutes, followed by placing on a wire netting. A 10 Kg weight is placed evenly on the absorbent material and the absorbent material allowed to drain for 20 minutes. The weight gain was then measured. The weight gain is defined as the absorption.

Re-wet Amount 50 ml of the synthetic urine is poured into the central part of the model diaper. After 10 minutes, 10 pieces of 10 cm×10 cm filter paper are stacked on the central part of the diaper, and a 3.5 Kg weight is placed evenly on the filter papers. The weight gain of the filter papers after 3 minutes is measured. The weight gain is defined as the re-wet amount. Smaller re-wet amount indicates improved dryness of the absorbent material.

EXAMPLE 1

76.6 g of sodium acrylate, 23 g of acrylic acid, 0.4 g of N,N'-methylenebisacrylamide, and 295 g of deionized water were charged into a one-liter glass reactor, stirred and mixed while the temperature of the contents maintained at 5° C.

After the dissolved oxygen content was reduced to 1 ppm or less by flowing nitrogen gas into the contents, 1 g of 1% aqueous solution of hydrogen peroxide, 1.2 g of 0.2% aqueous solution of ascorbic acid, and 2.4 g of 2% aqueous solution of 2,2'-azobisaminodipropane-di-hydrochloride were added and polymerized for about 5 hours to obtain the hydrogel polymer (I) containing 25% water absorbing resin.

400 parts by weight of the hydrogel polymer were added to a kneader and uniformly kneaded with 3 parts by weight of a 30% methanol solution of didecyldimethyammonium carbonate.

The kneaded mixture was vacuum dried at 90° C., and the dried mixture is ground with a pin mill. The particle size was then adjusted so that about 95% of the particles had a particle size of about 850–150 microns to obtain the anti-bacterial water absorbing agent (1). The results of measuring the performances of the anti-bacterial water absorbing agent (1) are shown in Tables 1 and 2.

EXAMPLE 2

An anti-bacterial water absorbing agent (2) was obtained in the same manner as in Example 1 except using 3 parts by weight of a 30% methanol solution of didodecyldimethyammonium carbonate instead of the 30% methanol solution of didecyldimethyammonium carbonate.

The results of measuring the performances of the anti-bacterial water absorbing agent (2) are shown in Tables 1 and 2.

EXAMPLE 3

A hydrogel material is obtained by allowing 100 parts of the commercially available water absorbing resin SANWET IM-1000 (available from Sanyo Chemical Industries, Japan; crosslinked copolymer of starch-sodium acrylate graft copolymer; the neutralized degree of 70 mole %) to absorb 400 parts of water and produce a hydrogel.

The resulting hydrogel material was uniformly kneaded with 3 parts by weight of 30% methanol solution of didecyldimethyammonium carbonate. The mixture was dried, ground, and the particle size was adjusted as in Example 1 to obtain an anti-bacterial water absorbing agent (3).

The results of measuring the performances of the anti-bacterial water absorbing agent (3) are shown in Tables 1 and 2.

EXAMPLE 4

100 parts by weight of the powder of the commercially available water absorbing resin SANWET IM-5800 (available from Sanyo Chemical Industries, Japan) was whipped in a kitchen mixer/blender, while progressively adding 4.5 parts by weight of didecyldimethylammonium carbonate (20% by weight of aqueous methanol solution; the ratio of methanol/water=50/50). SANWET IM-5800 is a surface-crosslinked sodium polyacrylate water absorbing resin having a neutralized degree of 72 mole %. The components were uniformly mixed to obtain the anti-bacterial water absorbing agent (4).

The results of measuring the performances of the anti-bacterial water absorbing agent (4) are shown in Tables 1 and 2.

EXAMPLE 5

An anti-bacterial water absorbing agent (5) was obtained in the same manner as in Example 4 except by using the same amount of octyltrimethylammonium carbonate instead of the 20% methanol solution of didecyldimethylammonium carbonate.

The results of measuring the performances of the anti-bacterial water absorbing agent (5) are shown in Tables 1 and 2.

EXAMPLES 6 AND 7

Anti-bacterial water absorbing agents (6) and (7) were obtained in the same manner as in Example 4 except using 0.45 part (Example 6) and 9 parts (Example 7) of a 20% aqueous methanol solution of didecyldimethylammonium carbonate.

The results of measuring the performances of the anti-bacterial water absorbing agent (6) and the anti-bacterial water absorbing agent (7) are respectively shown in Tables 1 and 2.

TEST EXAMPLE

The anti-bacterial water absorbing agents prepared in Examples 1, and 3 to 7 were used to produce water absorbent materials a–f, respectively as follows. Each water absorbing agent was distributed in the amount of 60 g/m$^2$ between two layers of pulp having a unit density of 100 g/m$^2$, followed by uniformly pressing the layers at a pressure of 5 Kg/m$^2$ to laminate the layers. Each of the resultant laminates was further provided with a polyethylene film on a lower lamination side and a non-woven fabric mainly composed of a polypropylene fiber on the upper lamination side. Each of the laminates were cut to a size of 14 cm (width) by 35 cm (length) to prepare the model diapers a–f, respectively.

The results of measuring the performances of these model diapers are shown in Table 3.

COMPARATIVE EXAMPLE 1

The hydrogel polymer prepared in Example 1 was vacuum dried at 90° C., and ground with a pin mill. The particle size was then adjusted to obtain about 95% of the particles having a particle size of about 850–150 microns.

The results of measuring the performances of the water absorbing resin powder are shown in Tables 1 and 2.

COMPARATIVE EXAMPLES 2 AND 3

The results of measuring the performances of the "SANWET IM-1000" and "SANWET IM-5800" are shown in Tables 1 and 2 as the Comparative Examples 2 and 3, respectively.

COMPARATIVE EXAMPLE 4

The anti-bacterial water absorbing agent was obtained in the same manner as in Example 1 except using the same amount of a 30% methanol solution of diethyldimethylammonium carbonate instead of the 30% methanol solution didecyldimethylammonium carbonate. The results of measuring the performances of the anti-bacterial water absorbing agent are shown in Tables 1 and 2.

COMPARATIVE EXAMPLES 5 AND 6

100 parts of the powder of the commercially available water absorbing resin SANWET IM-5800 available from Sanyo Chemical Industries, Japan is whipped in a kitchen mixer, while progressively adding 4.5 parts of 20% aqueous methanol solution of cetyltrimethylammonium chloride to obtain Comparative Example 5. 9 parts of 20% aqueous methanol solution of cetyltrimethyl-ammonium chloride was added to the resin to obtain Comparative Example 6. The ratio of methanol/water=50/50 in the aqueous methanol was % by weight. The components were uniformly mixed to obtain the anti-bacterial water absorbing agents. The results of measuring the performances of the anti-bacterial water absorbing agents are shown in Tables 1 and 2.

COMPARATIVE TEST EXAMPLE

Model diapers g-1 were prepared by the same process of Text Examples a–f except for using the water absorbing resin powders of Comparative Examples 1 to 6. The results of measuring the performances of these model diapers of the Comparative Test Examples are shown in Table 3.

TABLE 1

|  | Absorption | Anti-bacterial Test in *E. coli* (/ml) | | Powder flow property |
|---|---|---|---|---|
|  | (g/g) | After 2 hours | After 10 hours | (degree) |
| Example | | | | |
| 1 | 57 | 5.8 × 10 | 1.8 × 10 | 38 |
| 2 | 58 | 2.0 × 10$^2$ | 9.5 × 10 | 39 |
| 3 | 62 | 4.5 × 10 | 1.5 × 10 | 40 |
| 4 | 58 | <5 | <5 | 38 |
| 5 | 58 | 6.2 × 10$^2$ | 5.5 × 10$^3$ | 38 |
| 6 | 60 | 2.3 × 10$^2$ | 3.3 × 10$^3$ | 37 |
| 7 | 57 | 0 | 0 | 38 |
| Comparative Example | | | | |
| 1 | 57 | 3.2 × 10$^8$ | 4.1 × 10$^9$ | 38 |
| 2 | 62 | 4.8 × 10$^8$ | 5.4 × 10$^9$ | 40 |
| 3 | 60 | 2.1 × 10$^8$ | 3.0 × 10$^7$ | 37 |
| 4 | 57 | 8.8 × 10$^6$ | 6.2 × 10$^7$ | 38 |
| 5 | 53 | 2.3 × 10 | 1.2 × 10 | 47 |
| 6 | 56 | 1.5 × 10 | 5 | 52 |

TABLE 2

|  | Anti-bacterial Test in *Providencia vettgeri* (/ml) | |
|---|---|---|
|  | After 2 hours | After 10 hours |
| Example | | |
| 1 | 4.9 × 10$^2$ | 2.8 × 10$^2$ |
| 2 | 5.8 × 10$^2$ | 6.5 × 10$^2$ |
| 3 | 2.3 × 10$^2$ | 8.4 × 10 |

TABLE 2-continued

| | Anti-bacterial Test in *Providencia vettgeri* (/ml) | |
|---|---|---|
| | After 2 hours | After 10 hours |
| 4 | <5 | <5 |
| 5 | 7.8 × 10² | 9.5 × 10² |
| 6 | 4.1 × 10² | 1.8 × 10³ |
| 7 | 0 | 0 |
| Comparative Example | | |
| 1 | 6.3 × 10⁸ | 5.5 × 10⁹ |
| 2 | 7.7 × 10⁸ | 8.4 × 10⁹ |
| 3 | 7.5 × 10⁸ | 8.3 × 10⁹ |
| 4 | 2.0 × 10⁷ | 1.4 × 10⁸ |
| 5 | 1.6 × 10⁶ | 3.8 × 10³ |
| 6 | 1.1 × 10² | 4.2 × 10² |

TABLE 3

| Absorbent materials | Absorption (g/piece) | Re-wet amount (g) | Test for bad odor suppression |
|---|---|---|---|
| Test example | | | |
| a | 460 | 0.3 | 1.6 |
| b | 490 | 0.2 | 1.2 |
| c | 470 | 0.3 | 1.4 |
| d | 475 | 0.2 | 1.8 |
| e | 475 | 0.2 | 2.0 |
| f | 470 | 0.1 | 0.8 |
| Comparative test example | | | |
| g | 485 | 0.3 | 4.4 |
| h | 485 | 0.5 | 4.6 |
| i | 475 | 0.4 | 4.1 |
| j | 480 | 0.7 | 4.5 |
| k | 470 | 0.5 | 2.1 |
| l | 460 | 1.2 | 3.1 |

The data presented in Tables 1–3 demonstrate that the water absorption and re-wet amount are not significantly reduced by providing the polymeric resin with the quaternary ammonium cation. Furthermore, the resins having the quaternary ammonium groups show significant reduction in bacterial growth and significant reduction in the development of malodors.

The anti-bacterial water absorbing agent in accordance with the present invention has several advantages and effects. For example, the anti-bacterial water absorbing agent exhibits the excellent anti-bacterial effect in addition to the absorption performance, suppresses putrefaction by fungus, microorganisms, and bacterial of organic materials contained in urine, blood, and other body fluids absorbed in the water absorbing agent to inhibit the development of malodors.

In the conventional absorbent materials where the water absorbing resin and the anti-bacterial agent are mixed, the components may separate from each other by shaking or vibrations. The water absorbing resin or the anti-bacterial agent may partially sift through the absorbent fibrous layers. In the present invention, the anti-bacterial component is reacted with and fixed to the water absorbing resin of the present invention, thereby reducing the risk of separation of components from the finished product. Furthermore, the powder flow property is maintained with minimal dust generation. Incorporating the absorbent materials, such as disposable diapers and sanitary napkins provide an anti-bacterial function, thereby suppressing odors and the occurrence of skin irritation and rash.

The anti-bacterial water absorbing agent of the present invention is especially useful for various absorbent materials including disposable diapers for adults and infants, incontinence pads, sanitary napkins, panty liners, mother breat pads, nursing pads, after-parturition mats, and medical under pads. Further, the anti-bacterial water absorbing agent of the present invention is useful for an excretion treating agent and a gellation agent for various body fluids such as pet urine and waste blood which develop malodors due to putrefaction. The anti-bacterial water absorbing agent is also useful in the production of sheets or tapes of absorptive materials such as a pet sheet and a drip absorber. Further, the present invention is useful for the application employing gels prepared by allowing the anti-bacterial water absorbing resins to absorb water (e.g. cold retaining materials, artificial ice, and water beds), and the application involving odor development due to putrefaction such as sludge solidification agents and anti-dewing agents for walls.

Various details of the invention may be changed without departing from its spirit or scope. The foregoing description of the embodiments according to the present invention is provided for the purpose of illustration only, and not for the purpose of limiting the invention as defined by the appended claims and their equivalents.

What we claim is:

1. An anti-bacterial water absorbing agent comprising a water absorbing resin (A) having pendant acid groups, at least one acid group being in the form of a quaternary ammonium salt, and said resin (A) having a quaternary nitrogen atom content of about $2 \times 10^{-4}\%$ to about 0.8% by weight based on the molecular weight of said resin (A).

2. The anti-bacterial water absorbing agent according to claim 1, wherein the pendant acid group in the form of a quaternary ammonium salt has the formula (1):

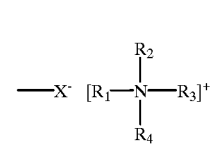

(1)

wherein —X⁻ is a pendant anionic group covalently bonded to a polymer backbone in the water absorbing resin (A), and $R_1$, $R_2$, $R_3$ and $R_4$ are organic groups; and at least one of $R_1$, $R_2$, $R_3$ and $R_4$ is a $C_5$ to $C_{20}$ aliphatic alkyl group.

3. The anti-bacterial water absorbing agent according to claim 2, wherein said water absorbing resin (A) is prepared by reacting a water absorbing resin (a) having pendant acid groups with a quaternary ammonium carbonate compound (b) in the presence of water.

4. The anti-bacterial water absorbing agent according to claim 3, wherein said resin (A) is prepared by mixing or kneading a hydrogel of said resin (a) with said quaternary ammonium carbonate compound (b) followed by heating to react and dry the mixture and grinding the resulting resin.

5. The anti-bacterial water absorbing agent according to claim 1, wherein said water absorbing resin (A) has an absorbency to physiological saline solution of 30 g/g or more.

6. A particulate anti-bacterial water absorbing agent comprising a water absorbing resin (A) having pendant acid groups, at least one acid group being in the form of a quaternary ammonium salt, and said resin (A) having a quaternary nitrogen atom content of about $2 \times 10^{-4}\%$ to about 0.8% by weight based on the molecular weight of said resin (A), wherein said resin (A) has a substantially dry particulate form having a particle size distribution of at least 90% by weight of 0.1–0.9 mm.

7. The anti-bacterial water absorbing agent according to claim 3, wherein about $3 \times 10^{-5}$ to about 0.3 equivalents of said quaternary ammonium carbonate (b) is reacted per equivalent of said acid groups in said resin (a).

8. The anti-bacterial water absorbing agent of claim 1, wherein said pendant acid groups in said resin (a) are selected from the group consisting of carboxyl, sulfonic, sulfuric and phosphoric groups, and neutralized groups thereof.

9. A method of producing an anti-bacterial water absorbing agent comprising the steps of reacting a water absorbing resin (a) having pendant acid groups with a quaternary ammonium carbonate compound (b) in the presence of water to produce said water absorbing resin (A) having pendant acid groups, at least one acid group being in the from of a quaternary ammonium salt, and having a quaternary nitrogen atom content of about $2 \times 10^{-4}\%$ to about 0.8% by weight based on the molecular weight of said resin (A).

10. The method of claim 9, wherein said pendant acid group in the form of a quaternary ammonium salt has the formula (1):

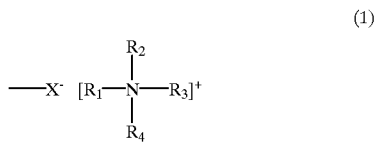

wherein —X⁻ is a pendant anionic group covalently bonded to a polymer backbone in the water absorbing resin (A); and $R_1$, $R_2$, $R_3$, and $R_4$ are organic groups: and at least one of $R_1$, $R_2$, $R_3$ and $R_4$ is a $C_5$ to $C_{20}$ aliphatic alkyl group.

11. The method of claim 9, wherein an aqueous solution of said quaternary ammonium carbonate compound (b) are mixed with a particle of said water absorbing resin (a) following by reacting said quaternary ammonium carbonate (b) with the surface of said particle of (a).

12. The method of claim 9, comprising mixing an aqueous solution of said quaternary ammonium carbonate compound (b) with particles of said water absorbing resin, followed by kneading the resulting hydrogel-forming mixture, and then heating to react and dry the hydrogel-forming mixture.

13. The method of claim 9, wherein said water absorbing resin (A) is produced by reacting about $3 \times 10^{-5}$ to about 0.3 equivalents of said quaternary ammonium carbonate per equivalent of said acid groups in the said water absorbing resin.

14. A water absorbent material comprising:

a water absorbent substrate; and an anti-bacterial water absorbing agent on or in said substrate, said anti-bacterial water absorbing agent comprising a water absorbing resin (A) having pendant acid groups, at least one acid group being in the form of a quaternary ammonium salt, and said resin (A) having a quaternary nitrogen atom content of about $2 \times 10^{-4}\%$ to about 0.8% by weight based on the molecular weight of said resin (A).

15. The water absorbent material of claim 14 wherein said substrate is a fibrous sheet material.

16. The water absorbent material of claim 14 wherein said substrate is a fibrous pulp.

17. The anti-bacterial water absorbing agent of claim 1, wherein said water absorbing agent is substantially dry particles and said resin comprises acrylic acid and an acrylate as resin constituent monomers.

18. The anti-bacterial water absorbing agent of claim 1, wherein said acid groups are carboxyl groups, and said resin contains about 20 mole % to about 50 mole % carboxyl groups based on the total of carboxyl and carboxylate groups in said resin.

19. The anti-bacterial water absorbing resin of claim 1, wherein said acid groups are carboxyl groups, and said resin contains about 25 mole % to about 40 mole % carboxyl groups based on the total of carboxyl and carboxylate groups in said resin.

20. The water absorbent material of claim 14, wherein said anti-bacterial water absorbing resin comprises acrylic acid and acrylate as resin constituent monomers.

21. The water absorbent material of claim 14, wherein said acid groups are carboxyl groups, and said resin contains about 20 mole % to about 50 mole % carboxyl groups based on the total carboxyl and carboxylate groups in said resin.

22. The water absorbent material of claim 14, wherein said water absorbent material is produced by the steps of applying dry particles of said anti-bacterial water absorbing agent between two layers of fibrous material and fusing the layers together.

23. The water absorbent material of claim 14, wherein said water absorbent material is produced by mixing heat fusible fibers with dry particles and said anti-bacterial water absorbing agent and fusing said fibers together.

* * * * *